United States Patent [19]

Akita et al.

[11] 4,008,362
[45] Feb. 15, 1977

[54] 1-N-((S)-α-SUBSTITUTED-ω-AMINOACYL)-NEAMINE OR -RIBOSTAMYCIN AND THE PRODUCTION THEREOF

[75] Inventors: Eiichi Akita, Kamakura; Tsutomu Tsuchiya, Yokohama; Shinichi Kondo, Yokohama; Shuntaro Yasuda, Yokohama; Sumio Umezawa, Tokyo; Hamao Umezawa, Tokyo, all of Japan

[73] Assignee: Meiji Seika Kaisha, Ltd., Tokyo, Japan

[22] Filed: Aug. 21, 1973

[21] Appl. No.: 390,217

[30] Foreign Application Priority Data

Aug. 25, 1972    Japan ............................ 47-84633

[52] U.S. Cl. ............................... 536/17; 424/180
[51] Int. Cl.² ............................................. C02H 9/02
[58] Field of Search ..... 260/210 AB, 210 E, 210 K, 260/210 R; 535/14

[56] References Cited
UNITED STATES PATENTS

| | | | |
|---|---|---|---|
| 3,781,268 | 12/1973 | Kawaguchi | 260/210 K |
| 3,792,037 | 2/1974 | Kawaguchi et al. | 260/210 AB |
| 3,925,354 | 12/1975 | Umezawa et al. | 260/210 AB |

OTHER PUBLICATIONS

Adams et al., Org. Reactions, vol. 12, pp. 172–173, 1962, Wiley & Sons, Inc., New York.
Moore et al., Azaserine," Synthetic Studies I J.A.C.S., vol. 76, pp. 2884, (1954).
Sidgwick, N.V. *The Org. Chem. of Nitrogen*, pp. 105–106, 1966, Clarendon Press, Oxford.
Royals, E. E., *Adv. Org. Chem.*, p. 600, 1954, Prentice-Hall, Inc., Englewood Cliff, N. J.
Fujisawa et al., "Aminoglycoside Antibiotics" J. of Antibiotics, vol. 27, No. 9, 1974, pp. 677–681.

*Primary Examiner*—Lewis Gotts
*Assistant Examiner*—Cary Owens
*Attorney, Agent, or Firm*—Larson, Taylor and Hinds

[57] ABSTRACT

An 1-N-((S)-α-substituted-ω-aminoacyl)-neamine or -ribostamycin of the formula

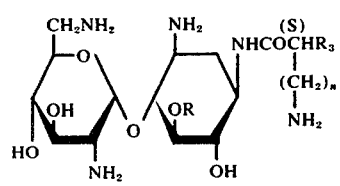

wherein R is a hydrogen atom or β-D-ribofuranosyl group of the formula

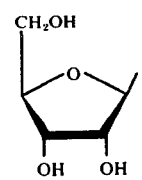

and $R_3$ is hydroxyl, amino-$NH_2$ or acylamino group —$NHR_4$ in which $R_4$ is an acyl group, and n is a whole number of 1 to 4, may be produced by subjecting the corresponding O-((S)-α-substituted-ω-aminoacyl)-neamine or -ribostamycin of the formula

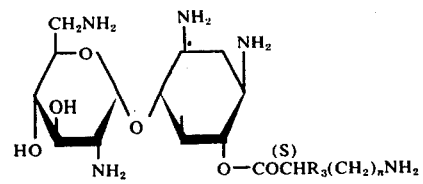

or its hydroxyl-masked and maino-masked form, to the action of a basic medium to produce an acyl-migration product of the formula:

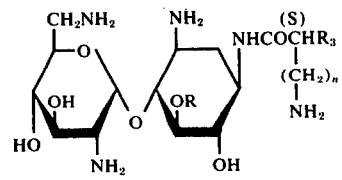

and, optionally converting the amino-masking groups into hydrogen atoms and also the hydroxyl-masking group into hydroge atom in a known manner if said amino-masking groups and said hydroxyl-masking groups are present in the acyl-migration product. The 1-N-((S)-α-substituted-ω-aminoacyl)-neamine or -ribostamycin produced is characterized by its useful activity inhibitory to the growth of bacteria resistant to the parent substance neamine or ribostamycin.

6 Claims, No Drawings

1-N-((S)-α-SUBSTITUTED-ω-AMINOACYL)-NEAMINE OR -RIBOSTAMYCIN AND THE PRODUCTION THEREOF

This invention relates to a process for the production of an 1-N-((S)-α-substituted -ω-aminoacyl)-neamine or -ribostamycin. This invention further relates to new and useful 1-N-((S)-α-substituted-ω-aminoacyl derivatives of neamine or ribostamycin produced by the process according to this invention.

It is known that butirosine are aminoglycosidic antibiotics produced by a microorganism Streptomyces species and are active against some kanamycin-resistant bacteria as well as against ribostamycin-resistant bacteria. Butirosin B has been identified as 1-N-((S)-α-hydroxy-γ-amino-n-butyryl)-ribostamycin (see "Tetrahedron Letters" Vol. 28, pages 2617–2630 (1971); and German "Offenlegungsschrift" No, 1914527). We have made our investigations in an attempt to provide a process of producing an 1-N-((S)-α-substituted-ω-aminoacyl)-neamine or -ribostamycin semi-synthetically starting from neamine or ribostamycin, as it is expected that the 1-N-((S)-α-substituted-ω-aminoacyl)-derivatives of neamine or ribostamycin are usefully effective even against some neamine-resistant bacteria and ribostamycin-resistant bacteria. Neamine (that is neomycin A) is a well known aminoglycosidic antibiotic. Ribostamycin is also a known aminoglycosidic antibiotic, originally designated as Antibiotic SF-733 (see "The Journal of Antibiotics" Vol. 23, No. 3, pages 155–161 (1970) No. 4, pages 173–183 (1970) and Japanese patent publication No. 17150/70). Neamine and ribostamycin may be represented by a general formula

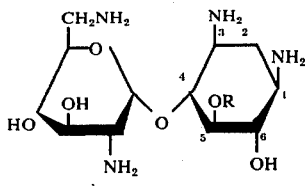

wherein R is a hydrogen atom or β-D-ribofuranosyl group of the formula

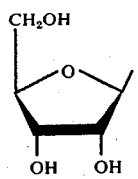

Neamine is shown by the above general formula (I) when R is a hydrogen atom, and ribostamycin is shown by the above general formula (I) when R is a β-D-ribofuranosyl group.

An object of this invention is to provide a new process according to which an 1-N-((S)-α-substituted-ω-aminoacyl)-neamine or -ribostamycin of a general formula

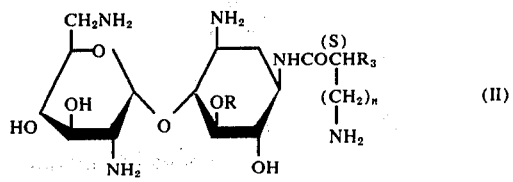

wherein R is a hydrogen atom or β-D-ribofuranosyl group and $R_3$ is a group —OH, —$NH_2$ or —$NHR_4$ in which $R_4$ is an acyl group, particularly an alkaroyl of 1–4 carbon atoms may be synthesized in a relatively simple way starting from neamine or ribostamycin, by introducing an (S)-α-substituted-ω-aminoacyl radical

preferentially in the 1-amino group of the neamine or ribostamycin molecule. The symbol (S) shown in the formula (II) is an expression of the steric configuration of organic compounds (see R. S. Cahn, C. K. Ingold & V. Prelog; "Experientia" Vol. 12, pages 81–94 (1956)). Further object of this invention is to provide new and useful semi-synthetic antibiotics which are derived from neamine or ribostamycin and characterized by their wide range of antibacterial spectra and low toxicity and hence are useful in chemotherapy of infections by various bacteria. Another objects of this invention will be clear from the following descriptions.

According to a first aspect of this invention, therefore, there is provided a process for the production of an 1-N-((S)-substituted-ω-aminoacyl)-neamine or -ribostamycin of the formula

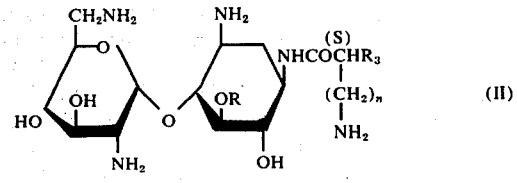

wherein R is a hydrogen atom or β-D-ribofuranosyl group of the formula

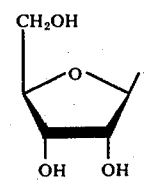

and $R_3$ is hydroxyl, amino —$NH_2$ or acylamino group —$NHR_4$ in which $R_4$ is an acyl group, and n is a whole number of 1 to 4, which comprises subjecting an O-((S)-α-substituted-ω-aminoacyl)-neamine or -ribostamycin of the formula:

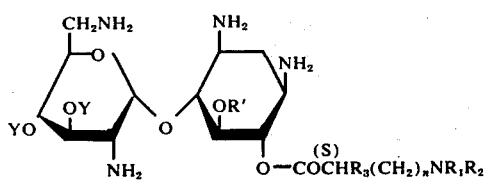

(III)

wherein R' is a hydrogen atom or a substituted or unsubstituted β-D-ribofuranosyl of the formula

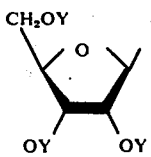

$R_1$ and $R_2$ are each a hydrogen atom or an amino-masking group selected from acyl, alkyloxycarbonyl, aralkyloxycarbonyl and aryloxycarbonyl group, or $R_1$ and $R_2$ together form a phthaloyl group, $R_3$ is hydroxyl, amino —$NH_2$ or an acylamino group —$NHR_4$ in which $R_4$ is an acyl group; and n is a whole number of 1 to 4; and Y is a hydrogen atom or a known hydroxyl-masking group such as an acyl group, for example, acetyl, benzoyl or benzyl, to the action of a basic medium to produce an acyl-migration product of the formula:

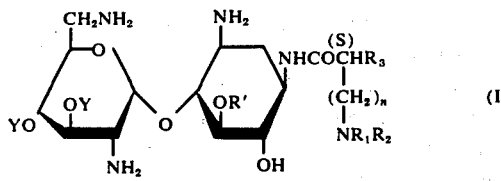

(IV)

wherein R', $R_1$, $R_2$, $R_3$, n and Y have the same meanings as defined above, and converting the amino-masking groups $R_1$, $R_2$ of the acyl-migration product (IV) into hydrogen atoms and also the hydroxyl-masking groups Y into hydrogen atom in a known manner when said amino-masking groups and said hydroxyl-masking groups remain in the acyl-migration product (IV).

In the process of this invention, the starting compound, that is, the O-((S)-α-substituted-ω-aminoacyl)-neamine or -ribostamycin of the formula (III) may be subjected to the action of a basic or alkaline medium by heating at an elevated temperature preferably in a range of 50° to 100° C a solution of the starting compound in water or an organic solvent therefor under basic or alkaline conditions which are provided by the presence of an organic base such as tertiary amine or hydrazine or an inorganic base such as an alkali metal hydroxide, for example, sodium or potassium hydroxide or carbonate or a basic anion-exchange resin in such a quantity enough to give the basicity or alkalinity to said solution. As the organic solvent there may be used a lower alkanol of 1–4 carbon atoms, for example, methanol, ethanol, butanol and propanol, either aqueous or anhydrous. When the starting compound of the formula (III) is subjected to the action of the basic medium in this way, there takes place such a reaction of rearrangement wherein the group —$COCHR_3(CH_2)_nNR_1R_2$ bonded through the ester-linkage to the hydroxyl group in the 6-position of the neamine or ribostamycin molecule of the starting compound is liberated therefrom and transferred to the amino group in the adjacent, 1-position of the neamine or ribostamycin molecule, producing the acyl-migration product of the formula (IV). In this reaction, it is seen that, in general, such an acyl group having been bonded through an ester-linkage to an hydroxyl group which exists in such a position adjacent to an amino group and in the "trans" relation to this amino group is readily transferred from said hydroxyl group to said amino group under the basic conditions. This fact has been discovered by the present inventors at the first time, and this discovery is the basis of the present invention.

It is known that, in general, an acyl group is likely to be bonded to a hydroxyl group under acidic conditions but is likely to be bonded to an amino group under basic conditions, so that the acyl group migrates from the hydroxyl group to the amino group when the nature of the environment medium containing the aforesaid different groups is reversed from acidity to basicity, and vice versa. This phenomena is known as "acyl migration" (see "Organic Reactions" Vol. 12, page 173, published from John Wiley & Sons, 1962). However, the acyl migration has never been utilised before the process of this invention for the purpose of introducing the acyl group in to an amino group existing in a particular position of a molecule when said molecule bears many amino groups.

In carrying out the process of this invention, the migration of the (S)-α-substituted-ω-aminoacyl group —$COCHR_3(CH_2)_nNR_1R_2$ takes place from the 6-hydroxyl group to the 1-amino group of the neamine or ribostamycin molecule of the starting compound (III) under the basic conditions. When the starting compound (III) contains further any acyl group for the $R_1$, $R_2$, $R_4$ and/or Y as described later, the acyl group may be liberated from the acyl-migration product (IV) during the process or by continuing the heating of the reaction mixture in the same basic medium, without isolating the acyl-migration product (IV), so that the conversion of the groups —OY of the acyl-migration product (IV) into hydroxyl group as well as the conversion of the acylamino group —$NR_1R_2$ or —$NHR_4$ into amino group —$NH_2$ occur in the same reaction mixture, giving immediately the final product (II).

When the starting compound (III) contains any hydroxyl-masking group other than the acyl group for the group Y as well as any other amino-masking group than the acyl group for the groups $R_1$ and/or $R_2$, it is necessary to further treat the acyl-migration product (IV) so as to convert the $R_1$, $R_2$ and Y groups of the acyl-migration product into hydrogen atoms in a known manner. For instance, when the hydroxyl-masking group Y is benzyl group and $R_1$ and/or $R_2$ are or is the amino-masking group such as alkyloxycarbonyl, aralkyloxycarbonyl or aryloxycarbonyl, particularly carbobenzoxy group in the starting compound (III), the acyl-migration product (IV) obtained still contains these hydroxyl-masking group and amino-masking groups and must be further treated so as to convert the hydroxyl-masking group and amino-masking groups into hydrogen atoms, respectively. Procedures for the conversion of these hydroxyl-masking group and amino-masking group into hydrogen are well known to the skilled in the art. For example, an acyl-migration product (IV) containing the benzyl group for the group Y and the carbobenzoxy group for the groups $R_1$ and $R_2$ may be subjected to simultaneous de-benzylation and de-carbobenzylation either by dissolving said product in a mixture of dioxane, acetic acid and water and hydrogenating it in the presence of palladium-carbon or by dissolving said product in liquid ammonia and treating this ammoniac solution with metallic sodium.

The O-((S)-α-substituted-ω-aminoacyl)-neamine or -ribostamycin of the formula (III) which is used as the starting compound in the process of the first aspect of this invention may be prepared from neamine or ribostamycin as the initial material in various ways. Thus, neamine or ribostamycin is at first reacted with such a reagent which is commonly used in the prior art of peptide synthesis to introduce a known amino-masking group into the four amino groups of the initial neamine or ribostamycin. The masking of the amino groups of neamine or ribostamycin may conveniently be effected by an acylation, carboalkoxylation or carbobenzoxylation of the amino groups of the initial material. For example, neamine or ribostamycin may be reacted with acetyl chloride, ethyl chloroformate or benzyl chloroformate to prepare the tetra-N-acetyl derivative, the tetra-N-ethoxycarbonyl derivative or the tetra-N-carbobenzoxy derivative of neamine or ribostamycin, respectively.

The tetra-N-acetyl derivative, tetra-N-ethoxycarbonyl derivative or tetra-N-carbobenzoxy derivative of neamine or ribostamycin so prepared may subsequently be treated in a known manner so as to mask or block all the hydroxyl groups other than the 6-hydroxyl group of said derivative with a known hydroxyl-masking group such as an acyl, isopropylidene, cyclohexylidene, benzylidene or benzyl. As an example of the tetra-N-carbobenzoxy derivative of ribostamycin of which all the hydroxyl groups other than the 6-hydroxyl group of said derivative have been protected by a known hydroxyl-masking group, there may be mentioned tetra-N-carbobenzoxy-3′, 4′ : 2″, 3″-dicyclohexylidene-5″-O-(1-methoxycyclohexyl)-ribostamycin of which preparation is described in the "Journal of Antibiotics" Vol. 25, No. 10, pages 613–616 (1972). The derivative having the masked hydroxyl groups so formed is then reacted with an (S)-α-substituted-ω-amino acid of the formula

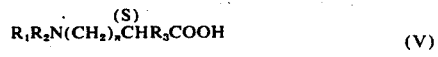

(V)

wherein $R_1$, $R_2$, $R_3$ and $n$ are as defined in the above, to prepare 6-O-((S)-α-substituted-ω-aminoacyl derivative of neamine or ribostamycin in which neamine or ribostamycin molecule the four amino groups have been masked by the amino-masking group and the hydroxyl groups also have been masked by the hydroxyl-masking groups. When this 6-O-((S)-α-substituted-ω-aminoacyl derivative so prepared is then treated in a known manner so as to convert the amino-masking groups into hydrogen atoms and, if desired, also all or part of the hydroxyl-masking groups into hydrogen atoms, there may be prepared the O-((S)-α-substituted-ω-aminoacyl)-neamine or -ribostamycin of the above formula (III).

When a compound containing both amino group and hydroxyl group in the molecule thereof is intended to be acetylated preferentially at the hydroxyl group, it has been proposed that the masking of the amino group is made by protonating said amino group with a strong organic acid such as trifluoroacetic acid so as to protect said amino group, and then the hydroxyl group may be acetylated preferentially using a usual acetylation reagent such as acetyl chloride or acetic anhydride or mixed anhydrides (see J. Bello & J. R. Vinograd; "Journal of American Chemical Society" Vol. 78, page 1369 (1956)). Using this method of protonating the amino group with a strong organic acid such as trifluoroacetic acid for the purpose of masking the amino groups of the initial neamine or ribostamycin, the O-((S)-α-substituted-ω-aminoacyl)-neamine or -ribostamycin of the formula (III) may also be prepared in the following way: The neamine or ribostamycin (the free base form) is dissolved in trifluoroacetic acid under ice-cooling and the resulting solution is admixed with ethyl ether to precipitate a trifluoroacetic acid salt of neamine or ribostamycin in which the four amino groups of the neamine or ribostamycin molecule have each been protected with the trifluoroacetic acid molecule. The neamine or ribostamycin trifluoroacetate so formed is then esterified or condensed with an (S)-α-substituted-ω-amino acid of the formula (V) in solution in dimethylformamide (DMF), acetone or tetrahydrofuran under ice-cooling and in the presence of a strong acid or a dehydrating agent such as dicyclohexylcarbodiimide. The acid of the formula (V) may conveniently be an (S)-α-substituted-ω-N-phthalimido acid according to the formula (V) wherein $R_1$ and $R_2$ together form a phthaloyl group. In the reaction (esterification) of the neamine or ribostamycin trifluoroacetate with the acid of the formula (V), all the hydroxyl groups, including the 6-hydroxyl group, of the neamine or ribostamycin molecule are attacked and have been O-aminoacylated at random by the acid of the formula (V), so that there is formed a mixture of mono-O-aminoacylated, di-O-aminoacylated, tri-O-aminoacylated and tetra-O-aminoacylated neamines in the form of their trifluoroacetate or a mixture of mono-O-aminoacylated to hexa-O-aminoacylated ribostamycins in the form of their trifluoroacetate. When this mixture of the O-aminoacylated neamines or ribostamycins in the form of their trifluoroacetate is neutralised by treating with a base, there gives the mixed O-aminoacylated neamines or ribostamycins which contain a 6-O-((S)-α-substituted-ω-aminoacyl)-neamine or -ribostamycin of the formula (III), as an intermediate. From the above-mentioned mixed O-aminoacylated neamines or ribostamycins may be isolated the 6-O-((S)-α-substituted-ω-aminoacyl)-neamine or -ribostamycin of the formula (III) in a chromatographic manner using, for example, cellulose powder, silica gel or a molecular sieve consisting of a three dimensional dextran network (commercially available under a trade name "Sephadex G-15", a product of Pharmacia Co., Sweden). The above-mentioned mixed O-aminoacylated neamines or ribostamycins containing the O-((S)-α-substituted-ω-aminoacyl)-neamine or -ribostamycins as such may be immediately employed for the starting material in the process of this invention, before or after the trifluoroacetic acid is liberated therefrom through the treatment with a base, as stated above. When said mixed O-aminoacylated neamines or ribostamycins are subjected to the action of the basic medium in the process of this invention, there are formed as the acyl-migration products mixed N-aminoacylated neamines or ribostamycins, including the desired 1-N-((S)-α-substituted-ω-aminoacyl)-neamine or -ribostamycin of the formula (II). The mixed N-aminoacylated neamines or ribostamycins formed as the acyl-migration products are then separated from the reaction mixture and dissolved in water to prepare an aqueous solution of them at pH about 8. This solution may then be subjected to a chromatographic separation in a column of CM-Sephadex C-25 (ammonium form) to isolate the desired 1-N-((S)-α-substituted-ω-aminoacyl)-neamine or -ribostamycin of the formula (II). Active fractions of the eluate issued from the column and containing the 1-N-((S)-α-substituted-ω-aminoacyl)-neamine or -ribostamycin can be detected by an oxidation test with periodic acid, as the presence of an 1-N-acyl substituent is detectable by said test (see "Tetrahedron Letters", Vol. 28, pages 2624–2628 (1971)).

According to a preferred embodiment of the first aspect of this invention, therefore, there is provided a process for the production of an 1-N-((S)-α-substituted-ω-aminoacyl)-neamine or -ribostamycin of the above formula (II), which comprises reacting 1 molar proportion of neamine or ribostamycin with 4 molar proportions of trifluoroacetic acid to prepare a salt of neamine or ribostamycin with trifluoroacetic acid where each of the four amino groups of the neamine or ribostamycin molecule has been associated with trifluoroacetic acid, esterifying the neamine or ribostamycin trifluoroacetate with an (S)-α-substituted-ω-amino acid derivative of the formula:

wherein $R'_1$ and $R'_2$ together form a phthaloyl group; $R_3$ is hydroxyl, amino group —$NH_2$ or phthalimido group or an acylamino group —$NHR_4$ in which $R_4$ is an acyl group preferably an alkaloyl group of 1–4 carbon atoms such as acetyl or phthaloyl; and $n$ is a whole number of 1, 2, 3 or 4, to prepare mixed O-(S)-α-substituted-ω-aminoacylated neamines or ribostamycins containing a compound of the formula:

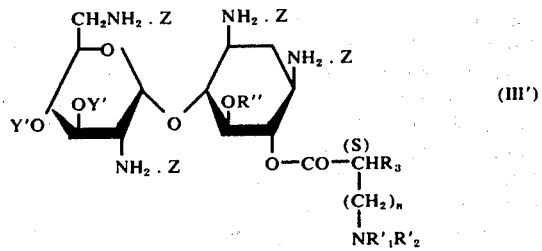

wherein $R'_1$, $R'_2$, $R_3$ and $n$ are as defined in the above; R″ is Y′ as defined below or a substituted β-D-ribofuranosyl of the formula:

and Y′ is a hydrogen atom or a group —$COCHR_3(CH_2)_nNR'_1R'_2$ and Z is trifluoroacetic acid, subjecting said mixed O-(S)-α-substituted-ω-aminoacylated neamines or ribostamycins to the action of a basic medium to produce acyl-migration products comprising a compound of the formula:

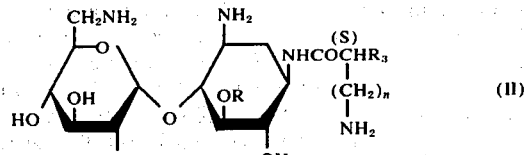

wherein R is a hydrogen atom or β-D-ribofuranosyl; and $R_3$ and $n$ are as defined in the above, separating the above acyl-migration products from the reaction mixture, and then isolating the compound of the formula (II) from the other acyl-migration products in a chromatographic manner.

When the neamine or ribostamycin trifluoroacetate is esterified by reacting with an (S)-α-substituted-ω-amino acid derivative of the formula (V′) in this preferred embodiment of the first aspect of this invention, it has been found preferable that 1 molar proportion of the neamine or ribostamycin trifluoroacetate is brought about into contact with 3–7 molar proportions of the (S)-α-substituted-ω-amino acid of the formula (V′).

When the compound of the formula (III′) is subjected to the action of the basic medium which may be provided by a solution of hydrazine in an aqueous ethanol according to the above-mentioned preferred embodiment of the first aspect of the invention, the migration of the O-(S)-α-substituted-ω-N-phthalimidoacyl substituent from the 6-hydroxyl group to the 1-amino group takes place advantageously with concurrent liberation of the trifluoroacetic acid as well as the phthaloyl group as the amino-masking group $R_1$ and $R_2$. This migration reaction may preferably be conducted at an elevated temperature of 50°–100° C.

The principal course of producing the final product of the formula (II) starting from neamine or ribostamycin according to the present invention may be represented schematically by the following equation:

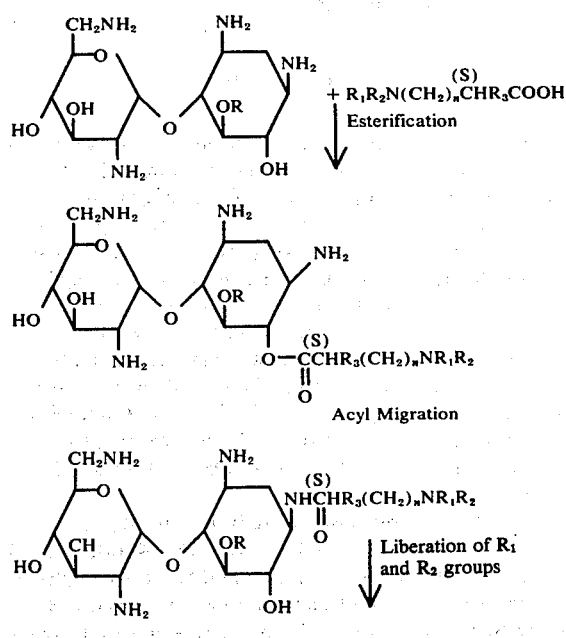

-continued

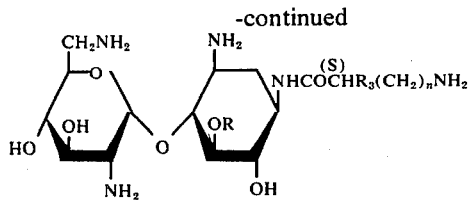

if the reactions for introducing the amino-masking groups and the hydroxyl-masking groups into the initial neamine or ribostamycin, the presence of the amino-masking and hydroxyl-masking groups in the reagents and in the intermediate products and the reactions for converting the amino-masking groups and hydroxyl-masking groups of the product into hydrogen atoms are omitted from the representation.

Among the amino acid of the formula (V) which is used in the process, an (S)-α-substituted-ω-amino acid of the formula (V) where $R_1$ and $R_2$ each are not the hydrogen atom but $R_3$ is hydroxyl group may conveniently be an (S)-α-hydroxy-ω-N-phthalimido acid or (S)-α-hydroxy-ω-N-carbobenzoxy-amino acid. An (S)-α-hydroxy-ω-N-phthanlimido acid of the formula

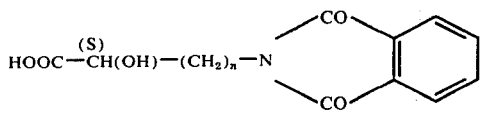

may be prepared by reacting a hydrochloride of an (S)-α,ω-diamino acid of the formula

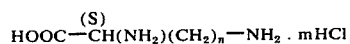

wherein m is a whole number of 1 or 2, with a basic copper carbonate in an alkaline aqueous solution to form the copper carboxylate, reacting this copper carboxylate with N-carboethoxyphthalimido to form a copper salt of (S)-α-amino-ω-N-phthalimido acid of the formula

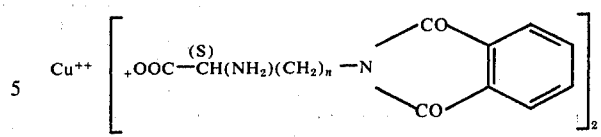

treating this copper salt with diluted hydrochloric acid in methanol to give the corresponding (S)-α-amino-ω-N-phthalimido acid hydrochloride and then reacting this hydrochloride with sodium nitrite in aqueous acetic acid to produce the desired (S)-α-hydroxy-ω-N-phthalimido acid. When the above-mentioned (S)-α-amino-ω-N-phthalimido acid hydrochloride prepared as an intermediate in the above procedure is acetylated with acetic anhydrides or acetyl chloride in a known manner, there may be prepared the corresponding (S)-α-N-acetylamino-ω-N-phthalimido acid, which may be employed as an (S)-α-substituted-ω-amino acid of the formula (V) in which $R_1$ and $R_2$ together form a phthaloyl group and $R_3$ is an acylamino group $—NHR_4$. When an (S)-α-substituted-ω-amino acid of the formula (V) wherein $R_1$ and $R_2$ are each hydrogen atom and $R_3$ is merely amino group $—NH_2$ is to be employed, it is convenient that this amino acid is phthaloylated in a known manner to give the corresponding (S)-α,ω-diphthaloylamino acid which is then used for the esterification of the neamine or ribostamycin.

When (S)-α-substituted-ω-amino acid of the formula (V) wherein $R_1$ and $R_2$ are the hydrogen atoms is to be used in the process, it is convenient to protect amino $NH_2$ groups of the compound merely by protonating by the strong organic acid, such as trifluoroacetic acid, to afford the solubility in organic solvents, as well as to decrease reactivity of the amino $NH_2$ groups.

The 1-N-((S)-α-substituted-ω-aminoacyl)-neamine or -ribostamycin obtained by the process of this invention is identifiable to be the 1-N-aminoacylated derivative of neamine or ribostamycin by the fact that when it is oxidised with periodic acid and then hydrolysed with 6N hydrochloric acid it gives 2-deoxystreptamine.

Some examples of the 1-N-((S)-α-substituted-ω-aminoacyl)-neamine or -ribostamycin produced by the process of this invention are listed in Table 1 below, together with their chemo-physical properties.

TABLE 1

| Compound | State | Melting point (° C) | [α] | PPC* | |
|---|---|---|---|---|---|
| 1-N-((S)-α-hydroxy-γ-amino-n-butyryl)-neamine | White powder | 130–198° (with decomp.) | +42° | $R_{neamine}$ | 0.44 |
| 1-N-((S)-α-hydroxy-δamino-n-valeryl)-neamine | " | 130–195° (with decomp.) | +41° | " | 0.50 |
| 1-N-((S)-α-hydroxy-ε-amino-n-caproyl)-neamine | " | — | +40° | " | 0.50 |
| 1-N-((S)-α,γ-diamino-n-butyryl)-neamine | " | — | — | " | 0.64 |
| 1-N-((S)-α-N-acetyl-α,γ-diamino-n-butyryl)-neamine | " | — | — | " | 0.59 |
| 1-N-((S)-α,δ-diamino-n-valeryl)-neamine | " | — | — | " | 0.5 |
| 1-N-((S)-α,ε-diamino-n-caproyl)-neamine | " | — | — | " | 0.44 |
| 1-N-((SR)-α-hydroxy-β-amino-n-propionyl)-ribostamycin | " | 160–198° (with decomp.) | — | $R_{ribostamycin}$ | 0.43 |
| 1-N-((S)-α-hydroxy-β-amino-n-propionyl)-ribostamycin | " | 195° (with decomp.) | — | $R_{ribostamycin}$ | 0.43 |
| 1-N-((S)-α-hydroxy- -amino-n-butyryl)-ribostamycin | " | 130–191° (with decomp.) | +34° | $R_{ribostamycin}$ | 0.47 |
| 1-N-((S)-α-hydroxy-δ-amino-n-valeryl)-ribostamycin | " | 130–195° (with decomp.) | +33° | $R_{ribostamycin}$ | 0.47 |
| 1-N-((S)-α-hydroxy-ε-amino-n-caproyl)-ribostamycin | Pale brown powder | — | +30° | $R_{ribostamycin}$ | 0.50 |
| 1-N-((S)-α,γ-diamino-n-buryryl)-ribostamycin | White powder | — | — | $R_{ribostamycin}$ | 0.61 |
| 1-N-((S)-α-N-acetyl-α,γ-diamino-n- | " | — | — | $R_{ribostamycin}$ | 0.59 |

TABLE 1-continued

| Compound | State | Melting point (° C) | [α] | PPC* |
|---|---|---|---|---|
| butyryl)-ribostamycin | | | | |

* In the column "PPC" of the Table 1, the figures given show the ratio of the distance of migration of the spot of each compound to that of neamine (this ratio is designatd as R$_{neamine}$) or the ratio of the distance of migration of the spot of each compound to that of ribostamycin (this ratio is designated as R$_{ribostamycin}$) when the compound is developed on paper-chromatogram using (6:4:1:3) n-butanol-pyridine-acetic acid-water as the developing solvent.

Among the compounds listed in Table 1, all the compounds other than 1-N-((S)-α-hydroxy-γ-amino-n-butyryl)-ribostamycin (namely, butirosin B) are new substances which are not described in any prior literature. According to a second aspect of this invention, therefore, there is provided a new substance of the formula

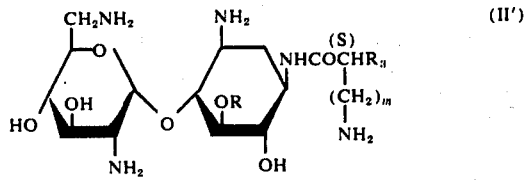

wherein R is a hydrogen atom or β-D-ribofuranosyl of the formula

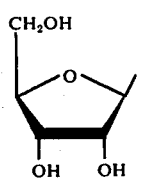

R$_3$ is hydroxyl, amino —NH$_2$ or an acylamino —NHR$_4$ in which R$_4$ is an acyl and particularly an alkanoyl of 1–4 carbon atoms such as acetyl, and $m$ is a whole number of 1, 3 or 4, when R is β-D-ribofuranosyl or $m$ is a whole number of 1, 2, 3 or 4 when R is a hydrogen atom.

According to a preferred embodiment of this second aspect of the invention, there is provided a new compound selected from the group consisting of 1-N-((S)-α-hydroxy-γ-amino-n-butyryl)-neamne, 1-N-((S)-α-hydroxy-δ-amino-n-valeryl)-neamine, 1-N-((S)-α-hydroxy-ε-amino-n-caproyl)-neamine, 1-N-((S)-α,γ-diamino-n-butyryl)-neamine, 1-N-((S)-α-N-acetyl-α,γ-diamino-n-butyryl)-neamine, 1-N-((S)-α,δ-diamino-n-valeryl)-neamine, 1-N-((S)-α,ε-diamino-n-caproyl)-neamine; 1-N-((SR)-α-hydroxy-β-amino-n-propyonyl)-ribostamycin, 1-N-((S)-α-hydroxy-β-amino-n-propionyl)-ribostamycin, 1-N-(SS)-α-hydroxy-δ-amino-n-valeryl)-ribostamycin, 1-N-((S)-α-hydroxy-ε-amino-n-caproyl)-ribostamycin, 1-N-((S)-α,γ-diamino-n-buryryl)-ribostamycin and 1-N-((S)-α-N-acetyl-α,γ-diamino-n-butyryl)-ribostamycin. Among them, 1-N-((S)-α-hydroxy-β-amino-n-propionyl)-ribostamycin, 1-N-((SR)-α-hydroxy-β-amino-n-propionyl)-ribostamycin, 1-N-((S)-α-hydroxy-γ-amino-n-butyryl)-neamine and 1-N-((S)-α-hydroxy-δ-amino-n-valeryl)-ribostamycin are most preferred, as these compounds exhibit wide range of antibacterial spectra and low toxicities and are very useful in the treatment of various bacterial infections. The new compound of the formula (II') according to this invention is active against gram-positive bacteria, gram-negative bacteria and acid-fast bacteria as well as against bacteria resistant to known antibiotics such as kanamycin, neamine and ribostamycin. The new compounds of the formula (II') of this invention is of low toxicity and exhibit a LD$_{50}$ value of 400–800 mg/kg in intravenous injection in mice.

The compounds of the formula (II') according to this invention are administered orally or intraperitoneally using any pharmaceutical form known to the art for such administration and in a similar manner to kanamycin and streptomycin. Examples of pharmaceutical forms for oral administration are powders, capsules, tablets, syrups, solution and the like.

Groups of mice each consisting of 10 mice of ICR series, 4-week-aged, male and with an average body weight of 22.5 g were inoculated by intraperitoneally injecting Pseudomonas aeruginosa IAM-1007 or Escherichia coli K-12 IAM 1254. Immediately after this inoculation, the infected mice were treated by intramuscular injection of the compound of this invention. Dose of 25–100 mg/kg of 1-N-((S)-α-hydroxy-γ-amino-n-butyryl)-neamine gave 90–100% survival of the P. aeruginosa infected mice at the end of 6 days after the inoculation and also 90–100% survival of the E. coli infected mice at the end of 7 days after the inoculation. In contrast, survival of the infected mice untreated was zero. The P. aeruginosa infected mice was treated similarly by intramuscular injection of 25–100 mg/kg of neamine or ribostamycin for the comparison purpose, when % survival of the so treated mice was zero, too. Groups of mice each consisting of 10 mice of ICR-JCL series, 4-week-aged, male and with an average g weight of 20.8 g. were inoculated intraperitoneally with Escherichia coli K-12 IAM 1264. Immediately after this inoculation, the infected mice was treated by intramuscularly injecting a dosage of 12.5–100 mg/kg of 1-N-((S)-α-hydroxy-δ-amino-n-valeryl)-ribostamycin. Rate of survival of the E. coli infected mice treated was 90–100%, whereas rate of survival of the infected mice untreated was only 10% at the end of 7 days after the inoculation.

Groups of mice each consisting of 10 mice of ICR series, 4-week aged, male and with an average body weight of 21.0 g were inoculated by intraperitoneally injecting Pseudomonas aeruginosa IAM-1007 or Escherichia coli K-12 IAM 1254. Immediately after this inoculation, the infected mice were treated by intramuscularly injecting a dosage of 25–100 mg/kg of 1-N-((SR)-α-hydroxy-β-amino-n-propionyl)-ribostamycin.

Rate of survival of the Pseudomonas aeruginosa or E. coli infected mice treated was 100%, whereas rate of survival of the infected mice untreated was only 10% at the end of 7 days after the inoculation. When treated with a dosage of 12.5 mg/kg of the compound, the rate of survival of the E. coli infected mice treated was 100%.

Groups of mice each consisting of 10 mice of ICR series 4 week-aged, male and with an average body weight of 21.8 g were inoculated by intraperitoneally injecting Pseudomonas aeruginosa IAM-1007 or Escherichia coli K-12 IAM 1254. Immediately after this inoculation, the infected mice were treated by intramuscularly injecting a dosage of 25–100 mg/kg of 1-N-((S)-α-hydroxy-β-amino-n-propionyl)-ribostamycin.

Rate of survival of the *Pseudomonas aeruginosa* or *Escherichia coli* infected mice treated was 100% whereas survival of the infected mice untreated was zero at the end of 7 days after the inoculation.

When treated with a dosage of 12.5 mg/kg of the compound the survival rate of the *E. coli* infected mice treated was 100%.

The invention is now illustrated with reference to the following Examples to which the present invention is not limited.

EXAMPLE 1

30 g. of ribostamycin (the free base form) was added to 127 ml. of trifluoroacetic acid under ice-cooling and stirring, and the mixture was allowed to stand at ambient temperature overnight. The resulting solution of amber color was admixed with 400 ml of ethyl ether, and the admixture was cooled to precipitate 69 g of a salt of ribostamycin with trifluoroacetic acid which was then removed by filtration. A 20 g. portion of this ribostamycin trifluoroacetate was taken and then dissolved in 250 ml of tetrahydrofuran together with 16.4 g. of (S)-α-hydroxy-γ-N-phthalimido-n-butyric acid of the formula

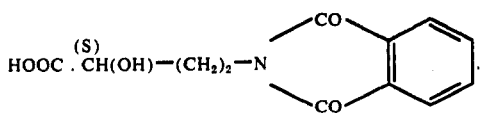

The solution was cooled with ice. A solution of 36.4 g of dicylcohexylcarbodiimide in 146 ml of tetrahydrofuran was prepared and cooled with ice. Both the solutions was combined together under ice-cooling and stirring. The combined solutions were agitated at ambient temperature for 2–3 hours and admixed with 8 ml of glacial acetic acid to decompose the excess of dicyclohexylcarbodiimide. 3286 mg of dicyclohexylurea produced was deposited and filtered off. The filtrate was concentrated to dryness, giving 43 g of a pale yellow colored solid comprising mixed trifluoroacetic acid salts of O-((S)-α-hydroxy-γ-N-phthalimido-n-butyryl)-ribostamycins.

This solid was then dissolved in 800 ml. of a liquid mixture of hydrazine hydrate and 80% aqueous ethanol (1:10 by volume), and the solution obtained was heated for 1 hour 30 minutes in an oil bath at 90°–100° C (When N-((S)-α-hydroxy-γ-amino-n-butyryl)-ribostamycins were formed with liberation of the phthaloyl groups). The reaction mixture was cooled to give a precipitate which was then filtered out. The precipitate was washed with 100 ml. of ethanol. The filtrate and the washings were combined together and concentrated to a hard syrup. This syrup was extracted with 100 ml of ethanol, then concentrated to dryness and again extracted with 180 ml of ethanol. The solid residue remaining after the ethanol extraction was admixed with the above-mentioned precipitate. The solid was then extracted with 100 ml of water. The ethanolic extract and the aqueous extract were combined together and diluted with water to a volume of 1000 ml (pH 8.0–8.2). This solution was passed into a column (38 by 276 mm; about 300 ml) of 40 g of CM-Sephadex C-25 (ammonium form) (CM-Sephadex C-25 essentially consisted of a three dimensional gel network of dextran afforded with carboxymethyl radical as the weakly acidic ion exchanger functional group. (C 25 is denser cross linked than C 50). The first running from the column was discarded and the column was washed successively with 1000 ml of water and 4 l. of 0.1N aqueous ammonia. The column was eluted using 0.2N aqueous ammonia and the eluate was collected in 20 ml fractions. The fractions No. 80 to No. 156 were combined together and the solution was concentrated under reduced pressure to give a crude product of 1-N-((S)-α-hydroxy-γ-amino-n-butyryl)-ribostamycin in a yield of 1.7 g. This crude product was again dissolved in 770 ml of water (pH 8.8–9.0), and this aqueous solution was passed into a similar column of 40 g. of CM-Sephadex C-25. After the column was washed with 1000 ml of water and 4 l. of 0.1N aqueous ammonia, the elution was made using 0.2N aqueous ammonia. The eluate was collected in 20 ml fractions and the fractions No. 68 to No. 128 were the active fractions. These active fractions were combined together and concentrated to give 1336 mg of a purified product of 1-N-((S)-α-hydroxy-γ-amino-n-butyryl)-ribostamycin.

Elemental analysis: Found: C 42.67, H 7.18, N 10.54%; Calculated for $C_{21}H_{41}N_5O_{12}\cdot 2H_2O$: C 42.7, H 7.63, N 11.85%

The antibacterial spectrum of this product to various microorganisms is shown in Table 2 below.

TABLE 2

| Test Microorganism | Incubation medium | Minimum Inhibitory concentration (mcg/ml) |
|---|---|---|
| Escherichia coli NIHJ | Heart infusion broth | 6.25 |
| Escherichia coli A3 | " | 6.25 |
| Escherichia coli K-12 U5/ML-1629 | " | 3.13 |
| Staphylococcus aureus 209P | " | 0.1 |
| Proteus vulgaris OX-19 | " | 3.13 |
| Pseudomonas aeruginosa IAM 1007 | " | 3.13 |
| Diplococcus pneumoniae | " | 0.2 |
| Escherichia coli K12 | Nutrient agar | 1.56 |
| Staphylococcus aureus 209P | " | 6.25 |
| Pseudomonas aeruginosa A3 | " | 25 |
| Pseudomonas aeruginosa No. 12 | " | 12.5 |
| Pseudomonas aeruginosa H9 | " | 6.25 |

When the product (the free base form) of this Example was intravenously injected in mice to estimate acute toxicity of the compound, it showed a $LD_{50}$ value of 690 mg/kg.

EXAMPLE 2

2 g of the ribostamycin trifluoroacetate prepared in the same manner as in Example 1 was taken and dissolved in 35 ml of a liquid mixture of tetrahydrofuran and dimethylformamide (10:1 by volume). This solution was admixed with a solution of 1.74 g of (S)-α-hydroxy-δ-N-phthalimido-n-valeric acid in 16 ml of tetrahydrofuran. A solution of 3.62 g of dicyclohexylcarbodiimide in 16 ml of tetrahydrofuran was added thereto under ice-cooling. The mixture was agitated for 30 minutes under ice-cooling and agitated at ambient temperature for 1 hour 25 minutes to effect the esterification of the hydroxyl groups of the ribostamycin with the substituted valeric acid. The reaction mixture was admixed with 0.8 ml of glacial acetic acid and allowed to stand at ambient temperature overnight to decompose the excess of dicyclohexylcarbodiimide. The dicylcohexylurea by-produced which precipitated was removed by filtration. The filtrate was concentrated to give a solid comprising mixed trifluoroacetic acid salts of O-((S)-α-hydroxy-δ-N-phthalimido-n-valeryl)-ribostamycins.

The solid so obtained was dissolved in 80 ml of a liquid mixture of hydrazine hydrate and 80% aqueous ethanol (1:10 by volume), and the solution was heated for 1 hour 30 minutes in an oil bath at 83° C. The reaction mixture as such was concentrated to dryness and the residue was extracted with 80 ml of water. The insoluble matters were filtered off, and the filtrate (the aqueous extract) at pH 8.2–8.4 was immediately passed into a column of 15.5 ml (about 2 g) of CM-Sephadex C-25 (ammonium form). The column was washed successively with 100 ml of water and with 600 ml of 0.1N aqueous ammonia. The elution was then made using 250 ml of 0.2N aqueous ammonia in the same manner as in Example 1. There was afforded 82.4 mg of a crude product of 1-N-((S)-α-hydroxy-δ-amino-n-valeryl)-ribostamycin. This crude product was again dissolved in water to give 20 ml of the aqueous solution (pH 8.4) which was then passed into a column of 15.5 ml (about 2 g) of CM-Sephadex C-25 (ammonium form). The column was washed successively with 50 ml of water and with 100 ml of 0.1N aqueous ammonia. The elution was made using 0.2N aqueous ammonia. The eluate was collected in 10 ml. fractions. The desired product was eluted in the fractions No. 29 to No. 44. These fractions were combined together and concentrated to give a pure product of 1-N-((S)-α-hydroxy-δ-amino-n-valeryl)-ribostamycin in a yield of 66.8 mg.

Elemental analysis: Found: C 44.34, H 7.28, N 11.67%; Calculated for $C_{22}H_{43}N_5O_{12}\cdot 2H_2O$: C 43.63, H 7.82, N 11.56%

The antibacterial spectrum of the product of this Example is shown in Table 3 below.

TABLE 3

| Test Microorganism | Incubation medium | Minimum Inhibitory concentration (mcg/ml) |
|---|---|---|
| Escherichia coli NIHJ | Heart infusion broth | 6.25 |
| Escherichia coli A3 | " | 6.25 |
| Escherichia coli K-12 U5/ML-1629 | " | 6.25 |
| Staphylococcus aureus 209P | " | 0.1 |
| Proteus vulgaris OX-19 | " | 6.25 |
| Pseudomonas aeruginosa IAM 1007 | " | 12.5 |
| Diplococcus pneumoniae | " | 0.39 |
| Escherichia coli K12 | Nutrient agar | 3.13 |
| Staphylococcus aureaus 209P | Nutrient agar | 3.13 |
| Pseudomonas aeruginosa A3 | " | 100 |
| Pseudomonas aeruginosa No. 12 | " | 50 |
| Pseudomonas aeruginosa H9 | " | 12.5 |

When the product (the free base form) of this Example was intravenously injected in mice, none of the mice died at a dosage of 600 mg/kg of this compound.

EXAMPLE 3

2 g of the ribostamycin trifluoroacetate prepared in the same manner as in Example 1 was taken and dissolved in 35 ml. of a liquid mixture of tetrahydrofuran and dimethylformamide (10:1 by volume). This solution was then mixed with a solution of 1.9 g of (S)-α-hydroxy-ε-N-phthalimido-n-caproic acid in 18 ml of tetrahydrofuran. To this mixture was then added a solution of 3.62 g of dicyclohexylcarbodiimide in 16 ml of tetrahydrofuran under ice-cooling. The resulting admixture was agitated for 30 minutes under ice-cooling and then agitated at ambient temperature for 1.5 hours to effect the esterification of the hydroxyl groups of ribostamycin with the substituted caproic acid. 0.8 ml of glacial acetic acid was added to the reaction mixture which was then allowed to stand at ambient temperature overnight to decompose the excess of dicyclohexylcarbodiimide. The formed dicyclohexylurea precipitated and was removed by filtration. The filtrate was concentrated to dryness, giving a solid comprising mixed trifluoroacetic acid salts of O-((S)-α-hydroxy-ε-N-phthalimido-n-caproyl)-ribostamycins.

The solid so obtained was dissolved in 80 ml of a liquid mixture of hydrazine hydrate and 80% aqueous ethanol (1:10 by volume), and the resulting solution was heated for 1.5 hours in a water bath at 83° C. The reaction mixture as such was concentrated to dryness, and the residue was extracted with 80 ml of water and the insoluble matter was filtered off. The filtrate (the aqueous extract) at pH 8.4 was passed into a column of 15.5 ml (about 2 g) of CM-Sephadex C-25 (ammonium form). The column was washed with 100 ml of water and then with 500 ml of 0.1N aqueous ammonia. After this, the elution was made using 300 ml of 0.2N aqueous ammonia, so that a crude product of 1-N-((S)-α-hydroxy-ε-amino-n-caproyl)-ribostamycin was obtained in a yield of 5 mg.

The antibacterial spectrum of this product against various microorganisms is shown in Table 4 below.

TABLE 4

| Test Microorganism | Incubation medium | Minimum Inhibitory concentration (mcg/ml) |
|---|---|---|
| Escherichia coli communis | Nutrient broth | 25 |
| Escherichia coli K-12 IAM 1264 | " | 6.25 |
| Staphylococcus aureus 209P | " | 6.25 |
| Pseudomonas aeruginosa IAM 1007 | " | More than 100 |
| Pseudomonas aeruginosa H-11 IAM 1007 | " | " |
| Klebsiella pneumoniae | " | 6.25 |
| Proteus vulgaris OX-19 | " | 12.5 |

EXAMPLE 4

774 mg of neamine (the free base form) was dissolved in 7.7 ml of trifluoroacetic acid under cooling with water. The solution so obtained was agitated for about 30 minutes and then admixed with 80 ml of ethyl ether to give 1545 mg of a precipitate consisting of the neamine trifluoroacetate which was then removed by filtration. 636 mg of this precipitate and 615 mg of (S)-α-hydroxy-γ-N-phthalimido-n-butyric acid were triturated together and then dissolved in 20 ml. of a liquid mixture of tetrahydrofuran and dimethylformamide (9:1 by volume). To this solution was added a solution of 1360 mg of dicyclohexylcarbodiimide in 5.44 ml of tetrahydrofuran under ice-cooling. The mixture was agitated for 30 minutes under ice-cooling and then agitated at ambient temperature for 2 hours 15 minutes to effect the esterification of the hydroxyl groups of neamine with the butyric acid. To the reaction mixture was added 0.3 ml of glacial acetic acid to decompose the excess of dicyclohexylcarbodiimide.

The mixture was allowed to stand overnight to precipitate the decomposition product dicyclohexylurea. The precipitate was filtered off and the filtrate was concentrated to give a solid comprising mixed trifluoroacetic acid salts of O-((S)-α-hydroxy-γ-N-phthaliimido-n-butyryl)-neamines.

This solid was dissolved in 30 ml of a mixture of hydrazine hydrate and 80% aqueous ethanol (1:10 by volume), and the resulting solution was heated for 1 hour 30 minutes in a water bath at 83° C. The reaction mixture was concentrated to dryness, the residue was extracted with 40 ml of water and the insoluble matter was filtered off. The filtrate (the aqueous extract) at pH 8.0 was passed into a column of 11 ml of CM-Sephadex C-25 (ammonium form). The column was washed with 50 ml. of water and then with 200 ml of 0.1N aqueous ammonia. The column was subsequently eluted using 0.2N aqueous ammonia. The eluate was collected in 10 ml. fractions and the desired product was eluted in the fractions No. 6 to No. 12. The active fractions were combined together and concentrated to give 1-N-((S)-α-hydroxy-δ-amino-n-butyryl)-neamine in a yield of 46.95 mg.

Elemental analysis: Found: C 42.8, H 7.50, N 14.86%; Calculated for $C_{16}H_{33}N_5O_8 \cdot 2H_2O$: C 43.5, H 7.93, N 15.86%

The antibacterial spectrum of this product against various microorganisms is shown in Table 5 below.

TABLE 5

| Test Microorganism | Incubation medium | Minimum Inhibitory concentrations (mcg/ml) |
|---|---|---|
| Escherichia coli K-12 | Nutrient agar | 6.25 |
| Staphylococcus aureus 209P | '' | 12.5 |
| Pseudomonas aeruginosa A3 | '' | 12.5 |
| Pseudomonas aeruginosa No.12 | '' | 12.5 |
| Pseudomonas aeruginosa H-9 | '' | 6.25 |

EXAMPLE 5

567 mg of the ribostamycin trifluoroacetate prepared in the same manner as in Example 1 was dissolved in a solution of 708 mg of (S)-α,γ-di-N-phthaloyl-2,4-diaminobutyric acid in 7 ml of tetrahydrofuran. The resulting solution was cooled with ice, and this ice-cooled solution was admixed wtih an ice-cooled solution of 1030 mg of dicylcohexylcarbodiimide in 4 ml of tetrahydrofuran under ice-cooling and stirring. The mixture so obtained was agitated for 30 minutes under ice-cooling and then agitated at ambient temperature for 2 hours 45 minutes to effect the esterification of the hydroxyl groups of ribostamycin with the butyric acid. 0.25 ml of glacial acetic acid was added to the reaction mixture to decompose the excess of dicyclohexylcarbodiimide. The insoluble dicyclohexylurea by-formed was filtered off, and the filtrate was concentrated to give a solid comprising mixed trifluoroacetic acid salt of O-((S)-α,γ-di-N-phthaloyl-2,4-diamino-butyryl)-ribostamycins.

This solid was dissolved in 27 ml of a liquid mixture of hydrazine hydrate and 80% aqueous ethanol (1:10 by volume), and the solution obtained was heated for 1.5 hours in a water bath at 83° C. The reaction mixture as such was concentrated to dryness, and the residue was extracted with 30 ml of water and the insoluble matter was filtered off. The filtrate (the aqueous extract) was passed into a column of 15 ml of CM-Sephadex C-25 (ammonium form). After the column was washed with 50 ml of water, the elution was made using 150 ml of 0.1N aqueous ammonia. A crude product of 1-N-((S)-α,δ-diamino-n-butyryl)-ribostamycin was obtained in a yield of 302 mg. This product inhibited the growth of Escherichia coli comnis on nutrient agar plate.

EXAMPLE 6

562 mg of the ribostamycin in trifluoroacetate prepared in the same manner as in Example 1 was dissolved in a solution of 536 mg of (S)-α-N-acetyl-γ-N-phthaloyl-2,4-diaminobutyric acid in 7 ml of tetrahydrofuran. The resulting solution was ice-cooled and then admixed with an ice-cooled solution of 1018 mg of dicyclohexylcarbodiimide in 4 ml of tetrahydrofuran under agitating and ice-cooling. The mixture was agitated for 30 minutes under ice-cooling and then agitated at ambient temperature for 1 hour to effect the esterification of the hydroxyl groups of ribostamycin with the substituted butyric acid. To the reaction mixture was added 0.25 ml of glacial acetic acid to decompose the dicyclohexylcarbodiimide. The insoluble dicyclohexylurea which precipitated was filtered off. The filtrate was concentrated to give a solid comprising mixture of trifluoroacetic acid salts of O-((S)-α-N-acetyl-γ-N-phthaloyl-2,4-diaminobutyryl)-ribostamycins.

This solid was dissolved in 26 ml of a liquid mixture of hydrazine hydrate and 80% aqueous ethanol (1:10 by volume), and the solution obtained was heated for 2 hours in a water bath at 83° C. The reaction mixture as such was concentrated to dryness, and the residue was extracted with 30 ml of water and the insoluble matter was filtered off. The filtrate (the aqueous extract) was passed into a column of 15 ml of CM-Sephadex CM-25 (ammonium form). The column was washed with 50 ml of water and eluted using 150 ml of 0.1N aqueous ammonia and 100 ml of 0.2N aqueous ammonia. The active fractions of the eluate were collected and concentrated to give a crude product of 1-N-((S)-α-N-acetyl-α,γ-diamino-n-butyryl)-ribostamycin in a yield of 330 mg. This product inhibited the growth of *Escherichia coli* commum's on nutrient agar plate.

EXAMPLE 7

1504.8 mg of the ribostamycin trifluoroacetate prepared in the same manner as in Example 1, and the trifluoroacetate of (SR)-α-hydroxy-β-amino-n-propionic acid prepared from 533 mg of (SR)-α-hydroxy-β-amino-n-propionic acid were dissolved in a mixture of 10 ml of tetrahydrofuran and 3.8 ml of dimethylformamide. The resulting solution was ice-cooled and then admixed with an ice-cooled solution of 2928 mg of dicyclohexylcarbodiimide in 10 ml of tetrahydrofuran under agitating and ice-cooling. The mixture was agitated for 2 hours under ice-cooling and then agitated at ambient temperature for 3 hours. The reaction mixture was left at ambient temperature overnight and then admixed with 1 ml of water and further stirred at ambient temperature for 9 hours and allowed to stand overnight at ambient temperature. The mixture was filtered and the filter cake was washed with 20 ml of tetrahydrofuran. The filtrate was combined with the tetrahydrofuran washings and the solution was concentrated to dryness to give a solid comprising mixed trifluoroacetic acid salts of O-((SR)-α-hydroxy-β-amino-n-propionyl)-ribostamycins. This solid was extracted with 30 ml of water and then with 10 ml of water and the insoluble solid matter was filtered off. The filtrate (the aqueous extract solution) was admixed with 20 ml of ethanol. The solution so obtained containing the mixed trifluoroacetic acid salt of O-((SR)-α-hydroxy-β-amino-n-propionyl)-ribostamycin was admixed with about 30 ml of strongly basic anion-exchange resin essentially consisting of a polystyrene having a quaternary ammonium groups-N—(CH$_3$)$_3$OH (commercially available under a registered trade name "Amberlite" IRA 400, Rohm & Haas Co., U.S.A.) (OH cycle), and the admixture was stirred for 4 hours at ambient temperature to effect the reaction in which the O-((SR)-α-hydroxy-β-amino-n-propionyl)-ribostamycins were converted into N-((SR)-α-hydroxy-β-amino-n-propionyl)-ribostamycins under the action of the basic nature of the anion-exchange resin. The reaction mixture was filtered and the filtration residue was washed with 50 ml of 40% aqueous ethanol. The filtrate was combined with the washings, and the solution so obtained was concentrated to dryness under reduced pressure to give 677.8 mg of a solid. This solid was dissolved in 100 ml of water and the resulting aqueous solution was passed into a column of 20 ml of CM-Sephadex C-25 (ammonium form). The column was washed with water and eluted with 0.2N aqueous ammonia. The eluated was collected in 5 ml fractions and the fractions No. 7 to No. 16 were combined together and concentrated to dryness under reduced pressure. The solid residue obtained was again dissolved in 100 ml of water and the solution was chromatographed in a similar column of CM-Sephadex C-25 using 0.1N aqueous ammonia as the developing solvent. The eluate was collected in 5 ml fractions and the fractions No. 14 to No. 19 were combined together. The solution was concentrated to dryness to give 289.1 mg of a crude product of 1-N-((SR)-α-hydroxy-β-amino-n-propionyl)-ribostamycin.

For purification, this crude product was dissolved in 50 ml of water and the aqueous solution obtained was again chromatographed in a column of 19 ml of CM-Sephadex C-25 using 0.05N aqueous ammonia as the developing solvent. The eluate was collected in 5 ml fractions. Just when the fraction No. 64 of the eluate had been collected, 0.1N aqueous ammonia was employed as the developing solvent in stead of the 0.05N aqueous ammonia. The fractions No. 69 to No. 72 were combined together and concentrated to dryness under reduced pressure to yield 30.03 mg of 1-N-((SR)-α-hydroxy-β-amino-n-propionyl)-ribostamycin.

Elemental analysis: Found: C 41.68, H 6.46, N 11.75%; Calculated for C$_{20}$H$_{39}$N$_5$O$_{12}$.2H$_2$O: C 41.6, H 7.46, N 12.1%

The antibacterial spectrum of this product against various microorganisms is shown in Table 6 below.

TALBE 6

| Microorganism | Incubation medium | Minimum Inhibitory concentration (mcg/ml) |
|---|---|---|
| Escherichia coli NIHJ | Nutrient agar | 3.12 |
| Escherichia coli K-12 | " | 1.56 |
| Staphylococcus aureus 209P | " | 6.25 |
| Pseudomonas aeruginosa A3 | " | 50 |
| Pseudomonas aeruginosa No.12 | " | 6.25 |
| Klebsiella pneumoniae | " | 3.12 |

TALBE 6-continued

| Microorganism | Incubation medium | Minimum Inhibitory concentration (mcg/ml) |
|---|---|---|
| PCI 602 | | |

When the product (the free base form) of this example was intravenously injected in mice to estimate acute toxicity of the compound, it showed a LD$_{50}$ of 650 mg/kg.

EXAMPLE 8

1560 mg of the ribostamycin trifluoroacetate prepared in the same manner as in Example 1, and the trifluoroacetate of (S)-α-hydroxy-β-amino-n-propionic acid prepared from 540 mg of (S)-α-hydroxy-β-amino-n-propionic acid were dissolved in a mixture of 12 ml of tetrahydrofuran and 4 ml of dimethylformamide. The resulting solution was ice-cooled and then admixed with an ice-cooled solution of 3002 mg of dicyclohexylcarbodiimide in 11 ml of tetrahydrofuran under agitating and ice-cooling. The mixture was agitated for 2 hours under ice-cooling and the agitated at ambient temperature for 3 hours. The reaction mixture was left at ambient temperature overnight and then admixed with 1 ml of water and further stirred at ambient temperature for 9 hours and allowed to stand overnight at ambient temperature. The mixture was filtered and the filter cake was washed with 20 ml of tetrahydrofuran. The filtrate was combined with the tetrahydrofuran washings and the solution was concentrated to dryness to give a solid comprising mixed trifluoroacetic acid salts of O-((S)-α-hydroxy-β-amino-n-propionyl)-ribostamycins. This solid was extracted with 30 ml of water and then with 10 ml of water and the insoluble solid matter was filtered off. The filtrate (the aqueous extract solution) was admixed with 21 ml of ethanol. The solution so obtained containing the mixed trifluoroacetic acid salts of O-((S)-α-hydroxy-β-amino-n-propionyl)-ribostamycin was admixed with about 32 ml of a strong basis anion-exchange resin essentially consisting of a polystyrene having quaternary ammonium groups-N(CH$_3$)$_3$OH (commercially available under a registered trade name Amberlite IRA 400, Rohm & Haas Co., U.S.A.) (OH cycle), and the admixture was stirred for 4 hours at ambient temperature to effect the reaction in which the O-((S)-α-hydroxy-β-amino-n-propionyl)-ribostamycins were converted into N-((S)-α-hydroxy-β-amino-n-propionyl)-ribostamycins under the action of the basic nature of the anion-exchange resin. The reaction mixture was filtered and the filtration residue was washed with 60 ml of 40% aqueous ethanol. The filtrate was combined with the washings, and the solution so obtained was concentrated to dryness under reduced pressure to give 685 mg of a solid. This was dissolved in 100 ml of water and the resulting aqueous solution was passed into a column of 20 ml of CM-Sephadex C-25 (ammonium form). The column was washed with water and eluted with 0.2N aqueous ammonia. The eluated was collected in 5 ml fractions and the fractions No. 7 to No. 18 were combined together and concentrated to dryness under reduced pressure. The solid residue obtained was again dissolved in 100 ml of water and the solution was chromatographed in a similar column of CM-Sephadex C-25 using 0.1N aqueous ammonia as the developing solvent. The eluate was collected in 5 ml fractions and the fractions No. 13 to No. 20 were combined together. The solution was concentrated to dryness to give 275 mg of a crude product of 1-N-((S)-α-hydroxy-β-amino-n-propionyl)-ribostamycin.

For purification, this crude product was dissolved in 50 ml of water and the aqueous solution obtained was again chromatographed in a column of 20 ml of CM-Sephadex C-25 using 0.05N aqueous ammonia as the developing solvent. The eluate was collected in 5 ml fractions. Just when the fraction No. 66 of the eluate had been collected, 0.1N aqueous ammonia was employed as the developing solvent instead of the 0.05N aqueous ammonia. The fractions No. 70 to No. 73 were combined together and concentrated to dryness under reduced pressure to yield 42.1 mg of 1-N-((S)-α-hydroxy-β-amino-n-propionyl)-ribostamycin.

Elemental analysis: Found: C 41.71, H 6.81, N 7.81 Calculated for $C_{20}H_{39}N_5O_{12} \cdot 2 H_2O$: C 41.6, H 7.46, N 12.1%

The antibacterial spectrum of this product against various microorganisms is shown in Table 7 below.

TABLE 7

| Microorganism | Incubation medium | Minimum Inhibitory concentration (mcg/ml) |
|---|---|---|
| Escherichia coli NIHJ | Nutrient agar | 3.12 |
| Escherichia coli K-12 | " | 1.56 |
| Staphylococcus aureus 209P | " | 3.12 |
| Pseudomonas aeruginosa A3 | " | 50 |
| Pseudomonas aeruginosa No.12 | " | 6.25 |
| Klebsiella pneumoniae PCI 602 | " | 1.56 |

When the product (the free base form) of this example was intravenously injected in mice to estimate acute toxicity of the compound, it showed a $LD_{50}$ of 650 mg/kg.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages conditions.

What we claim is:
1. A substance of the formula:

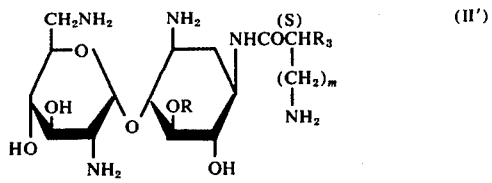

(II')

wherein R is a hydrogen atom or β-D-ribofuranosyl of the formula

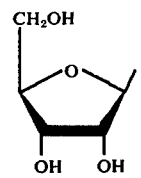

$R_3$ is hydroxyl, $-NH_2$ or $-NHR_4$ in which $R_4$ is an alkanoyl of 1–4 carbon atoms, and m is a whole number of 1, 3 or 4, when R is β-D-ribofuranosyl and m is a whole number of 1, 2, 3, or 4 when R is a hydrogen atoms.

2. A substance according to claim 1 and selected from the group consisting of 1-N-((S)-α-hydroxy-γ-amino-n-butyryl)-neamine, 1-N-((S)-α-hydroxy-δ-amino-n-valeryl)-neamine, 1-N-((S)-α-hydroxy-ε-amino-n-caproyl)-neamine, 1-N-((S)-α,γ-diamino-n-butyryl)-neamine, 1-N-((S)-α-N-acetyl-α,γdiamino-n-butyryl)-neamine, 1-N-((S)-α,δ-diamino-n-valeryl)-neamine, 1-N-((S)-α,ε-diamino-n-caproyl)-neamine; 1-N-((SR)-α-hydroxy-β-amino-n-propyonyl)-ribostamycin, 1-N-((S)-α-hydroxy-β-amino-n-propionyl)-ribostamycin, 1-N-((S)-α-hydroxy-δ-amino-n-valeryl)-ribostamycin, 1-N-((S)-α-hydroxy-ε-amino-n-caproyl)-ribostamycin, 1-N-((S)-α,γ-diamino-n-butyryl)-ribostamycin and 1-N-((S)-α-N-acetyl-α,γ-diamino-n-butyryl)-ribostamycin.

3. 1-N-((S)-α-Hydroxy-δ-amino-n-valeryl)-ribostamycin.

4. 1-N-((S)-α-Hydroxy-γ-amino-n-butyryl)-neamine.

5. 1-N-((S)-α-Hydroxy-β-amino-n-propionyl)-ribostamycin.

6. 1-N-((S)-α-Hydroxy-β-amino-n-propionyl)-ribostamycin.

* * * * *